United States Patent
Verin et al.

(10) Patent No.: US 6,616,629 B1
(45) Date of Patent: Sep. 9, 2003

(54) MEDICAL APPLIANCE WITH CENTERING BALLOON

(75) Inventors: Vitali Verin, Geneva (CH); Youri Popowski, Geneva (CH)

(73) Assignee: Schneider (Europe) A.G., Buelach (CH)

( * ) Notice: Subject to any disclaimer, the term of this patent is extended or adjusted under 35 U.S.C. 154(b) by 0 days.

(21) Appl. No.: 09/332,657

(22) Filed: Jun. 14, 1999

Related U.S. Application Data

(63) Continuation of application No. 08/492,503, filed on Jun. 20, 1995, now Pat. No. 5,976,106.

(30) Foreign Application Priority Data

Jun. 24, 1994 (EP) .............................................. 94109858

(51) Int. Cl.[7] .............................................. A61M 29/00
(52) U.S. Cl. ...................................... 604/101.05; 600/1
(58) Field of Search ........................ 604/96.01, 97–104, 604/264; 600/1, 34

(56) References Cited

U.S. PATENT DOCUMENTS

| | | |
|---|---|---|
| 1,442,051 A | 1/1923 | Cummings |
| 2,546,761 A | 3/1951 | Loftus .......................... 128/1.2 |
| 2,862,108 A | 11/1958 | Meilink ........................ 250/106 |
| 2,955,208 A | 10/1960 | Stevens ........................ 250/108 |
| 3,060,924 A | 10/1962 | Rush ........................... 128/1.2 |
| 3,147,383 A | 9/1964 | Prest ........................... 250/108 |
| 3,324,847 A | 6/1967 | Zoumboulis ................. 128/1.2 |
| 3,505,991 A | 4/1970 | Hellerstein et al. ........... 128/1.1 |
| 3,643,096 A | 2/1972 | Jeffries, Jr. et al. ...... 250/108 R |
| 3,669,093 A | 6/1972 | Sauerwein et al. ........... 128/1.1 |
| 3,674,006 A | 7/1972 | Holmer ........................ 128/1.2 |
| 3,750,653 A | 8/1973 | Simon .......................... 128/1.2 |
| 3,811,426 A | 5/1974 | Culver et al. ................. 128/1.2 |
| 3,861,380 A | 1/1975 | Chassagne et al. ........... 128/1.2 |
| 3,866,050 A | 2/1975 | Whitfield ..................... 250/497 |
| 3,927,325 A | 12/1975 | Hungate et al. .............. 250/435 |

(List continued on next page.)

FOREIGN PATENT DOCUMENTS

| | | |
|---|---|---|
| CA | 2166915 A | 8/1996 |
| DE | 3620123 A1 | 12/1987 |

(List continued on next page.)

OTHER PUBLICATIONS

Fackelmann, "Harbinger of a Heart Attack", *Science News*, vol. 151, Jun. 14, 1997, pp. 374–375.

Lommatzsch et al., "Radiation effects on the optic nerve observed after brachytherapy of choroidal melanomas with 106Ru/106Rh plaques", *Graefe's Arch. Clin. Exp. Ophthalmology* vol. 232, pp. 482–487, 1994.

(List continued on next page.)

*Primary Examiner*—Anhtuan T. Nguyen
*Assistant Examiner*—Ann Y. Lam
(74) *Attorney, Agent, or Firm*—Christensen O'Connor Johnson Kindness PLLC

(57) ABSTRACT

The balloon catheter comprises a catheter tube surrounded distally by an elongated inflatable balloon. Throughout the catheter tube is a longitudinal lumen for positioning a radioactive radiation emitter within the balloon. The catheter comprises a second lumen for directing inflation fluid into the balloon. Belt means creating a waist are mounted on the balloon to squeeze it down to nearly the diameter of the catheter thereby leaving a small passage for the inflation fluid. The belt means divide the balloon into sections to assure a close center fit of the catheter within the balloon.

30 Claims, 2 Drawing Sheets

U.S. PATENT DOCUMENTS

| | | | |
|---|---|---|---|
| 3,970,073 A | 7/1976 | Greene | 128/1.2 |
| 4,096,862 A | 6/1978 | DeLuca | 128/348 |
| 4,220,864 A | 9/1980 | Sauerwein et al. | 250/497 |
| 4,225,790 A | 9/1980 | Parsons, Jr. et al. | 250/497 |
| 4,244,357 A | 1/1981 | Morrison | 128/1.2 |
| 4,281,252 A | 7/1981 | Parsons, Jr. et al. | 250/497 |
| 4,314,157 A | 2/1982 | Gaines | 250/497 |
| 4,364,376 A | 12/1982 | Bigham | 128/1.1 |
| 4,573,966 A | 3/1986 | Weikl et al. | |
| 4,581,017 A | 4/1986 | Sahota | 604/101 |
| 4,584,991 A | 4/1986 | Tokita et al. | 128/1.1 |
| 4,588,395 A | 5/1986 | Lemelson | 604/59 |
| 4,631,415 A | 12/1986 | Sauerwein et al. | 250/497.1 |
| 4,697,575 A | 10/1987 | Horowitz | 128/1.2 |
| 4,702,228 A | 10/1987 | Russell, Jr. et al. | 128/1.2 |
| 4,706,652 A | 11/1987 | Horowitz | 128/1.2 |
| 4,754,752 A * | 7/1988 | Ginsburg et al. | 128/303.12 |
| 4,763,642 A | 8/1988 | Horowitz | 128/1.2 |
| 4,763,671 A | 8/1988 | Goffinet | 128/786 |
| 4,782,834 A | 11/1988 | Maguire et al. | 128/344 |
| 4,784,116 A | 11/1988 | Russell, Jr. et al. | 128/1.2 |
| 4,815,449 A | 3/1989 | Horowitz | 600/7 |
| 4,819,618 A | 4/1989 | Liprie | 600/7 |
| 4,851,694 A | 7/1989 | Rague et al. | 250/497.1 |
| 4,861,520 A | 8/1989 | van't Hooft et al. | 252/644 |
| 4,881,937 A | 11/1989 | van't Hooft et al. | 600/3 |
| 4,897,076 A | 1/1990 | Puthawala et al. | 600/7 |
| 4,921,483 A | 5/1990 | Wijay et al. | |
| 4,936,823 A | 6/1990 | Colvin et al. | 600/7 |
| 4,963,128 A | 10/1990 | Daniel et al. | 600/7 |
| 4,969,863 A | 11/1990 | van't Hooft et al. | 600/3 |
| 4,976,266 A | 12/1990 | Huffman et al. | 128/659 |
| 4,976,680 A | 12/1990 | Hayman et al. | 600/7 |
| 4,976,690 A | 12/1990 | Solar et al. | 604/96 |
| 4,983,167 A | 1/1991 | Sahota | 606/194 |
| 5,019,042 A * | 5/1991 | Sahota | 604/101 |
| 5,030,194 A | 7/1991 | Van't Hooft | 600/3 |
| 5,032,113 A | 7/1991 | Burns | 604/96 |
| 5,059,166 A | 10/1991 | Fischell et al. | 600/3 |
| 5,074,845 A * | 12/1991 | Miraki et al. | 604/101 |
| 5,084,001 A | 1/1992 | Van't Hooft et al. | 600/3 |
| 5,084,002 A | 1/1992 | Liprie | 600/7 |
| 5,090,958 A | 2/1992 | Sahota | 604/98 |
| 5,092,834 A | 3/1992 | Bradshaw et al. | 600/7 |
| 5,103,395 A | 4/1992 | Spako et al. | 364/413.26 |
| 5,106,360 A | 4/1992 | Ishiwara et al. | 600/2 |
| 5,120,973 A | 6/1992 | Rohe et al. | 250/497.1 |
| 5,139,473 A | 8/1992 | Bradshaw et al. | 600/3 |
| 5,141,487 A * | 8/1992 | Liprie | |
| 5,147,282 A | 9/1992 | Kan | 600/1 |
| 5,147,377 A | 9/1992 | Sahota | 606/194 |
| 5,160,321 A | 11/1992 | Sahota | 604/96 |
| 5,163,896 A | 11/1992 | Suthanthiran et al. | 600/8 |
| 5,176,617 A | 1/1993 | Fischell et al. | 600/3 |
| 5,183,455 A | 2/1993 | Hayman et al. | 600/7 |
| 5,199,939 A * | 4/1993 | Dake et al. | |
| 5,213,561 A | 5/1993 | Weinstein et al. | 600/7 |
| 5,267,960 A | 12/1993 | Hayman et al. | 604/106 |
| 5,282,781 A | 2/1994 | Liprie | 600/3 |
| 5,302,168 A | 4/1994 | Hess | 600/3 |
| 5,312,343 A | 5/1994 | Krog et al. | |
| 5,320,605 A | 6/1994 | Sahota | 604/101 |
| 5,344,383 A | 9/1994 | Liping | 600/3 |
| 5,354,257 A | 10/1994 | Roubin et al. | 600/7 |
| 5,370,608 A | 12/1994 | Sahota et al. | 604/20 |
| 5,370,617 A | 12/1994 | Sahota | 604/102 |
| 5,370,685 A | 12/1994 | Stevens | 623/2 |
| 5,391,139 A | 2/1995 | Edmundson | 600/7 |
| 5,395,300 A | 3/1995 | Liprie | 600/3 |
| 5,405,309 A | 4/1995 | Carden, Jr. | 600/3 |
| 5,409,015 A | 4/1995 | Palermo | 128/772 |
| 5,411,466 A | 5/1995 | Hess | 600/3 |
| 5,417,653 A | 5/1995 | Sahota et al. | 604/20 |
| 5,425,720 A | 6/1995 | Rogalsky et al. | 604/198 |
| 5,429,582 A | 7/1995 | Williams | 600/2 |
| 5,484,384 A | 1/1996 | Fearnot | 600/3 |
| 5,498,227 A | 3/1996 | Mawad | 600/3 |
| 5,503,613 A | 4/1996 | Weinberger | 600/3 |
| 5,503,614 A | 4/1996 | Liprie | 600/7 |
| 5,532,122 A | 7/1996 | Drukier | 435/5 |
| 5,538,494 A | 7/1996 | Matsuda | 600/1 |
| 5,540,659 A | 7/1996 | Teirstein | 604/104 |
| 5,556,389 A | 9/1996 | Liprie | 604/264 |
| 5,575,749 A | 11/1996 | Liprie | 600/3 |
| 5,605,530 A | 2/1997 | Fischell et al. | 600/3 |
| 5,611,767 A | 3/1997 | Williams | 600/2 |
| 5,616,114 A | 4/1997 | Thornton et al. | 600/3 |
| 5,618,266 A | 4/1997 | Liprie | 604/21 |
| 5,624,372 A | 4/1997 | Liprie | 600/3 |
| 5,643,171 A | 7/1997 | Bradshaw et al. | 600/1 |
| 5,649,924 A | 7/1997 | Everett et al. | 606/15 |
| 5,653,683 A | 8/1997 | D'Andrea | 604/21 |
| 5,662,580 A | 9/1997 | Bradshaw et al. | 600/3 |
| 5,674,177 A | 10/1997 | Hehrlein et al. | 600/3 |
| 5,683,345 A | 11/1997 | Waksman et al. | 600/3 |
| 5,688,220 A * | 11/1997 | Verin et al. | 600/1 |
| 5,707,332 A | 1/1998 | Weinberger | 600/3 |
| 5,713,828 A | 2/1998 | Coniglione | 600/7 |
| 5,720,717 A | 2/1998 | D'Andrea | 604/21 |
| 5,722,984 A | 3/1998 | Fischell et al. | 606/198 |
| 5,728,042 A | 3/1998 | Schwager | 600/3 |
| 5,730,698 A | 3/1998 | Fischell et al. | 600/3 |
| 5,772,642 A * | 6/1998 | Ciamacco, Jr. et al. | 604/280 |
| 5,782,740 A | 7/1998 | Schneiderman | 600/1 |
| 5,782,742 A | 7/1998 | Crocker et al. | 600/3 |
| 5,795,286 A | 8/1998 | Fischell et al. | 600/3 |
| 5,800,333 A | 9/1998 | Liprie | 600/3 |
| 5,803,895 A | 9/1998 | Kronholz et al. | 600/3 |
| 5,807,231 A | 9/1998 | Liprie | 600/3 |
| 5,816,259 A | 10/1998 | Rose | 128/898 |
| 5,816,999 A | 10/1998 | Bischoff et al. | 600/3 |
| 5,820,553 A | 10/1998 | Hughes | 600/426 |
| 5,833,593 A | 11/1998 | Liprie | 600/3 |
| 5,840,008 A | 11/1998 | Klein et al. | 600/3 |
| 5,840,009 A | 11/1998 | Fischell et al. | 600/3 |
| 5,840,064 A | 11/1998 | Liprie | 604/96 |
| 5,843,163 A | 12/1998 | Wall | 623/1 |
| 5,849,036 A | 12/1998 | Zarate | 623/1 |
| 5,851,171 A | 12/1998 | Gasson | 600/3 |
| 5,851,172 A | 12/1998 | Bueche et al. | 600/7 |
| 5,855,546 A | 1/1999 | Hastings et al. | 600/3 |
| 5,857,956 A | 1/1999 | Liprie | 600/7 |
| 5,863,284 A | 1/1999 | Klein | 600/3 |
| 5,863,285 A | 1/1999 | Coletti | 600/3 |
| 5,865,720 A | 2/1999 | Hastings et al. | 600/3 |
| 5,871,436 A | 2/1999 | Eury | 600/3 |
| 5,871,437 A | 2/1999 | Alt | 600/3 |
| 5,873,811 A | 2/1999 | Wang et al. | 600/5 |
| 5,879,282 A | 3/1999 | Fischell et al. | 600/3 |
| 5,882,290 A | 3/1999 | Kume | 600/3 |
| 5,882,291 A | 3/1999 | Bradshaw et al. | 600/3 |
| 5,891,091 A | 4/1999 | Teirstein | 604/104 |
| 5,897,573 A | 4/1999 | Rosenthal et al. | 606/224 |
| 5,899,882 A | 5/1999 | Waksman et al. | 604/96 |
| 5,906,573 A | 5/1999 | Aretz | 600/3 |
| 5,910,101 A | 6/1999 | Andrews et al. | 600/3 |
| 5,910,102 A | 6/1999 | Hastings | 600/3 |
| 5,913,813 A | 6/1999 | Williams et al. | 600/3 |
| 5,916,143 A | 6/1999 | Apple et al. | 600/3 |
| 5,919,126 A | 7/1999 | Armini | 600/3 |
| 5,924,973 A | 7/1999 | Weinberger | 600/3 |

| Patent No. | Date | Inventor | Class |
|---|---|---|---|
| 5,924,974 A | 7/1999 | Loffler | 600/3 |
| 5,925,353 A | 7/1999 | Mosseri | 424/178.1 |
| 5,938,582 A | 8/1999 | Ciamacco, Jr. et al. | 600/3 |
| 5,947,889 A | 9/1999 | Hehrlein | 600/3 |
| 5,947,924 A | 9/1999 | Liprie | 604/96 |
| 5,947,958 A | 9/1999 | Woodard et al. | 606/15 |
| 5,957,829 A | 9/1999 | Thornton | 600/3 |
| 5,961,439 A | 10/1999 | Chernomorsky et al. | 600/4 |
| 5,967,966 A | 10/1999 | Kronholz et al. | 600/3 |
| 5,971,909 A | 10/1999 | Bradshaw et al. | 600/3 |
| 5,976,106 A * | 11/1999 | Verin et al. | 604/96 |
| 5,997,462 A | 12/1999 | Loffler | 600/3 |
| 5,997,463 A | 12/1999 | Cutrer | 600/8 |
| 6,010,445 A | 1/2000 | Armini et al. | 600/3 |
| 6,013,019 A | 1/2000 | Fischell et al. | 600/3 |
| 6,013,020 A | 1/2000 | Meloul et al. | 600/7 |
| 6,019,718 A | 2/2000 | Hektner | 600/3 |
| 6,024,690 A | 2/2000 | Lee et al. | 600/3 |
| 6,030,333 A | 2/2000 | Sioshansi et al. | 600/3 |
| 6,033,357 A | 3/2000 | Ciezki et al. | 600/3 |
| 6,048,300 A | 4/2000 | Thornton et al. | 600/7 |
| 6,050,930 A | 4/2000 | Teirstein | 600/3 |
| 6,053,858 A | 4/2000 | Bueche et al. | 600/3 |
| 6,059,713 A | 5/2000 | Urick et al. | 600/3 |
| 6,059,752 A | 5/2000 | Segal | 604/107 |
| 6,059,812 A | 5/2000 | Clerc et al. | 606/198 |
| 6,066,083 A | 5/2000 | Slater et al. | 600/8 |
| 6,068,611 A | 5/2000 | Loffler et al. | 604/101 |
| 6,071,227 A | 6/2000 | Popowski et al. | 600/3 |
| 6,074,338 A | 6/2000 | Popwski et al. | 600/3 |
| 6,077,213 A | 6/2000 | Ciezki et al. | 600/3 |
| 6,090,035 A | 7/2000 | Campbell et al. | 600/7 |
| 6,093,142 A | 7/2000 | Ciamacco, Jr. | 600/3 |
| 6,095,966 A | 8/2000 | Chornenky et al. | 600/3 |
| 6,099,455 A | 8/2000 | Columbo et al. | 600/3 |
| 6,099,499 A | 8/2000 | Ciamacco, Jr. | 604/103 |
| 6,106,454 A | 8/2000 | Berg et al. | 600/3 |
| 6,110,097 A | 8/2000 | Hastings et al. | 600/3 |
| 6,117,064 A | 9/2000 | Apple et al. | 600/3 |
| 6,117,065 A | 9/2000 | Hastings et al. | 600/3 |
| 6,120,533 A | 9/2000 | Fischell | 623/1.11 |
| 6,132,358 A | 10/2000 | Glenn et al. | 600/3 |
| 6,132,423 A | 10/2000 | Aita et al. | 606/7 |
| 6,142,926 A * | 11/2000 | Schneiderman | 600/3 |
| 6,146,322 A | 11/2000 | Papirov et al. | 600/3 |
| 6,146,323 A | 11/2000 | Fischell | 600/3 |
| 6,149,574 A | 11/2000 | Trauthen et al. | 600/3 |
| 6,149,575 A | 11/2000 | Leonhardt | 600/4 |
| 6,152,869 A | 11/2000 | Park et al. | 600/3 |
| 6,159,139 A | 12/2000 | Chiu | 600/3 |
| 6,159,140 A | 12/2000 | Loeffler et al. | 600/3 |
| 6,159,142 A | 12/2000 | Alt | 600/3 |
| 6,159,143 A | 12/2000 | Lennox | 600/4 |
| 6,162,165 A | 12/2000 | Apple et al. | 600/3 |
| 6,176,821 B1 | 1/2001 | Crocker et al. | 600/3 |
| 6,179,768 B1 | 1/2001 | Loffler et al. | 600/7 |
| 6,179,789 B1 | 1/2001 | Tu et al. | 600/585 |
| 6,183,409 B1 | 2/2001 | Armini | 600/3 |
| 6,183,410 B1 | 2/2001 | Jacobsen et al. | 600/3 |
| 6,187,037 B1 | 2/2001 | Satz | 623/1.34 |
| 6,192,271 B1 | 2/2001 | Hayman | 604/21 |
| 6,196,963 B1 | 3/2001 | Williams | 600/3 |
| 6,196,964 B1 | 3/2001 | Loffler et al. | 600/7 |
| 6,196,996 B1 | 3/2001 | Teirstein | 604/104 |
| 6,200,256 B1 | 3/2001 | Weinberger | 600/3 |
| 6,200,257 B1 | 3/2001 | Winkler | 600/3 |
| 6,200,307 B1 | 3/2001 | Kasinkas et al. | 606/7 |
| 6,203,485 B1 | 3/2001 | Urick | 600/3 |
| 6,210,312 B1 | 4/2001 | Nagy | 600/3 |
| 6,210,313 B1 | 4/2001 | Eury | 600/3 |
| 6,210,315 B1 | 4/2001 | Andrews et al. | 600/7 |
| 6,210,316 B1 | 4/2001 | Slater et al. | 600/8 |
| 6,213,976 B1 | 4/2001 | Trerotola | 604/104 |
| 6,224,535 B1 | 5/2001 | Chiu et al. | 600/3 |
| 6,224,536 B1 | 5/2001 | Pike | 600/3 |
| 6,231,494 B1 | 5/2001 | Verin et al. | 600/1 |
| 6,231,495 B1 | 5/2001 | Denk | 600/1 |
| 6,231,719 B1 | 5/2001 | Garvey et al. | 162/109 |
| 6,234,951 B1 | 5/2001 | Hastings et al. | 600/3 |
| 6,234,952 B1 | 5/2001 | Liprie | 600/3 |
| 6,238,332 B1 | 5/2001 | Kanesaka | 600/3 |
| 6,248,057 B1 | 6/2001 | Mavity et al. | 600/3 |
| 6,251,059 B1 | 6/2001 | Apple et al. | 600/3 |
| 6,254,552 B1 | 7/2001 | Lewis et al. | 600/603 |
| 6,258,019 B1 | 7/2001 | Verin et al. | 600/1 |
| 6,264,596 B1 | 7/2001 | Weadock | 600/3 |
| 6,267,775 B1 | 7/2001 | Clerc et al. | 606/198 |

FOREIGN PATENT DOCUMENTS

| | | |
|---|---|---|
| DE | 9102312.2 | 8/1992 |
| DE | 195 26 680 A1 | 1/1997 |
| DE | 197 54 870 A1 | 8/1998 |
| DE | 197 24 233 C1 | 12/1998 |
| DE | 197 58 234 | 7/1999 |
| DE | 198 07 727 | 7/1999 |
| DE | 198 25 563 | 12/1999 |
| DE | 198 25 999 | 12/1999 |
| DE | 198 26 000 | 12/1999 |
| DE | 198 29 444 | 1/2000 |
| DE | 198 29 447 | 1/2000 |
| EP | 0 152 124 | 8/1985 |
| EP | 0 158 630 | 10/1985 |
| EP | 0 433 011 A1 | 6/1991 |
| EP | 0 447 745 A2 | 9/1991 |
| EP | 0 466 681 A1 | 1/1992 |
| EP | 0 474 994 | 3/1992 |
| EP | 0 514 913 A2 | 11/1992 |
| EP | 0 633 041 A1 | 1/1995 |
| EP | 0 686 342 A1 | 12/1995 |
| EP | 0 688 580 A1 | 12/1995 |
| EP | 0 696 906 B1 | 2/1996 |
| EP | 0 749 764 A1 | 12/1996 |
| EP | 0 754 472 A2 | 1/1997 |
| EP | 0 754 473 A2 | 1/1997 |
| EP | 0 593 136 B1 | 3/1997 |
| EP | 0 778 051 A1 | 6/1997 |
| EP | 0 801 961 A2 | 10/1997 |
| EP | 0 810 004 | 12/1997 |
| EP | 0810004 | 12/1997 |
| EP | 0 409 436 | 7/1998 |
| EP | 0 629 380 B1 | 7/1998 |
| EP | 0 865 803 | 9/1998 |
| EP | 0865803 | 9/1998 |
| EP | 0 904 798 | 3/1999 |
| EP | 0904798 | 3/1999 |
| EP | 0904799 | 3/1999 |
| EP | 0 904 799 | 3/1999 |
| JP | 1071210 | 3/1998 |
| JP | 10071210 | 3/1998 |
| JP | 2000014810 | 1/2000 |
| JP | 2000024001 | 1/2000 |
| JP | 20000241001 | 1/2000 |
| WO | WO 86/03124 | 6/1986 |
| WO | WO 92/00776 | 1/1992 |
| WO | WO 93/04735 | 3/1993 |
| WO | WO 94/25106 | 11/1994 |
| WO | WO 94/26205 | 11/1994 |
| WO | WO 95/07732 | 3/1995 |
| WO | WO 95/19807 | 7/1995 |
| WO | WO 96/06654 | 3/1996 |
| WO | WO 96/10436 | 4/1996 |
| WO | WO 96/13303 | 5/1996 |

| | | | | | | |
|---|---|---|---|---|---|---|
| WO | WO 96/14898 | 5/1996 | | WO | WO 99/44687 | 9/1999 |
| WO | WO 96/17654 | 6/1996 | | WO | WO 99/49935 | 10/1999 |
| WO | WO 96/22121 | 7/1996 | | WO | WO 99/56825 | 11/1999 |
| WO | WO 96/29943 | 10/1996 | | WO | WO 99/56828 | 11/1999 |
| WO | WO 96/40352 | 12/1996 | | WO | WO 99/61107 | 12/1999 |
| WO | WO 97/07740 | 3/1997 | | WO | WO 99/62598 | 12/1999 |
| WO | WO 97/09937 | 3/1997 | | WO | WO 99/66979 | 12/1999 |
| WO | WO 97/17029 | 5/1997 | | WO | WO 0003292 | 1/2000 |
| WO | WO 97/18012 | 5/1997 | | WO | WO 00/03292 | 1/2000 |
| WO | WO 97/19706 | 6/1997 | | WO | WO 00/04838 | 2/2000 |
| WO | WO 97/25102 | 7/1997 | | WO | WO 0004838 | 2/2000 |
| WO | WO 97/25103 | 7/1997 | | WO | WO 0004953 | 2/2000 |
| WO | WO 97/40889 | 11/1997 | | WO | WO 00/04953 | 2/2000 |
| WO | WO 98/01183 | 1/1998 | | WO | WO 00/09212 | 2/2000 |
| WO | WO 98/01184 | 1/1998 | | WO | WO 0009212 | 2/2000 |
| WO | WO 98/01185 | 1/1998 | | WO | WO 0029501 | 5/2000 |
| WO | WO 98/01186 | 1/1998 | | WO | WO 00/29501 | 5/2000 |
| WO | WO 98/11936 | 3/1998 | | WO | WO 00/32271 | 6/2000 |
| WO | WO 98/16151 | 4/1998 | | WO | WO 00/37137 | 6/2000 |
| WO | WO 98/20935 | 5/1998 | | WO | WO 00/45627 | 8/2000 |
| WO | WO 98/25674 | 6/1998 | | WO | WO 00/45892 | 8/2000 |
| WO | WO 98/29049 | 7/1998 | | WO | WO 00/54836 | 9/2000 |
| WO | WO 98/30273 | 7/1998 | | WO | WO 00/56249 | 9/2000 |
| WO | WO 98/34681 | 8/1998 | | WO | WO 00/57956 | 10/2000 |
| WO | WO 98/36788 | 8/1998 | | WO | WO 00/67845 | 11/2000 |
| WO | WO 98/36790 | 8/1998 | | WO | WO 00/69503 | 11/2000 |
| WO | WO 98/36796 | 8/1998 | | WO | WO 00/74778 | 12/2000 |
| WO | WO 98/39052 | 9/1998 | | WO | WO 00/76557 | 12/2000 |
| WO | WO 98/39062 | 9/1998 | | WO | WO 00/78394 | 12/2000 |
| WO | WO 98/39063 | 9/1998 | | WO | WO 00/78395 | 12/2000 |
| WO | WO 98/40032 | 9/1998 | | WO | WO 01/14011 | 3/2001 |
| WO | WO 98/46309 | 10/1998 | | WO | WO 01/14617 | 3/2001 |
| WO | WO 98/55179 | 12/1998 | | WO | WO 01/21106 | 3/2001 |
| WO | WO 98/57706 | 12/1998 | | WO | WO 01/21245 | 3/2001 |
| WO | WO 99/01179 | 1/1999 | | WO | WO 01/21248 | 3/2001 |
| WO | WO 99/02219 | 1/1999 | | WO | WO 01/26734 | 4/2001 |
| WO | WO 99/04706 | 2/1999 | | | | |
| WO | WO 99/04856 | 2/1999 | | | | |
| WO | WO 99/10045 | 3/1999 | | | | |
| WO | WO 99/21615 | 5/1999 | | | | |
| WO | WO 99/21616 | 5/1999 | | | | |
| WO | WO 99/22774 | 5/1999 | | | | |
| WO | WO 99/22775 | 5/1999 | | | | |
| WO | WO 99/22812 | 5/1999 | | | | |
| WO | WO 99/22815 | 5/1999 | | | | |
| WO | WO 99/24116 | 5/1999 | | | | |
| WO | WO 99/24117 | 5/1999 | | | | |
| WO | WO 99/29354 | 6/1999 | | | | |
| WO | WO 99/29370 | 6/1999 | | | | |
| WO | WO 99/29371 | 6/1999 | | | | |
| WO | WO 99/30779 | 6/1999 | | | | |
| WO | WO 99/34969 | 7/1999 | | | | |
| WO | WO 99/36121 | 7/1999 | | | | |
| WO | WO 99/39628 | 8/1999 | | | | |
| WO | WO 99/40962 | 8/1999 | | | | |
| WO | WO 99/40970 | 8/1999 | | | | |
| WO | WO 99/40971 | 8/1999 | | | | |
| WO | WO 99/40972 | 8/1999 | | | | |
| WO | WO 99/40973 | 8/1999 | | | | |
| WO | WO 99/40974 | 8/1999 | | | | |
| WO | WO 99/42162 | 8/1999 | | | | |
| WO | WO 99/42163 | 8/1999 | | | | |
| WO | WO 99/42177 | 8/1999 | | | | |
| WO | WO 99/44686 | 9/1999 | | | | |

OTHER PUBLICATIONS

*Radiotherapy of Intraoculare and Orbital Tumors,* Springer–Verlak publishers, Berlin Heidelberg and New York, copyright 1993, pp. 23–30 and 363–367.

Raloff, "Nuclear Medicine Gets Friendlier—Experimental Therapies Seek to Poison Just the Disease", *Science News,* Bol. 152, Jul. 19, 1997, pp. 40–41.

Sealy, R. et al., "The Treatment of Cancer of the Uvula and Soft Palate with Interstitial Radioactive Wire Implants," *Int. J. Radiation Oncology Biol. Phys.,* vol. 10, Oct. 1984, pp. 1951–1955.

Sinclair, W.K. et al. "Artificial Radioactive Sources for Interstitial Therapy," *The British Journal of Radiology,* Aug. 1952, pp. 417–419.

Wallace, D.M. et al., "Radioactive Tantalum Wire Implantation as a Method of Treatment for Early Carcinoma of the Bladder," *The British Journal of Radiology,* Aug. 1952, pp. 421–424.

Sutherland, "Managing Cancer Through Synergy", *Administrative Radiology Journal,* Nov. 1996, pp. 21–27.

Tjho–Heslinga et al., "Results of ruthenium irradiation of uveal melanona", *Radiotherapy Oncology,* vol. 29, pp 33–38, 1993.

\* cited by examiner

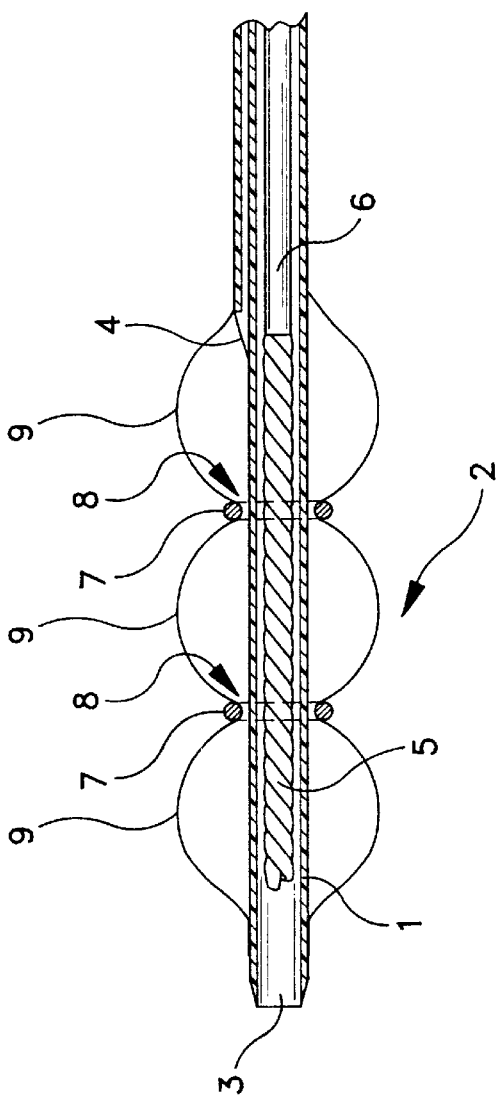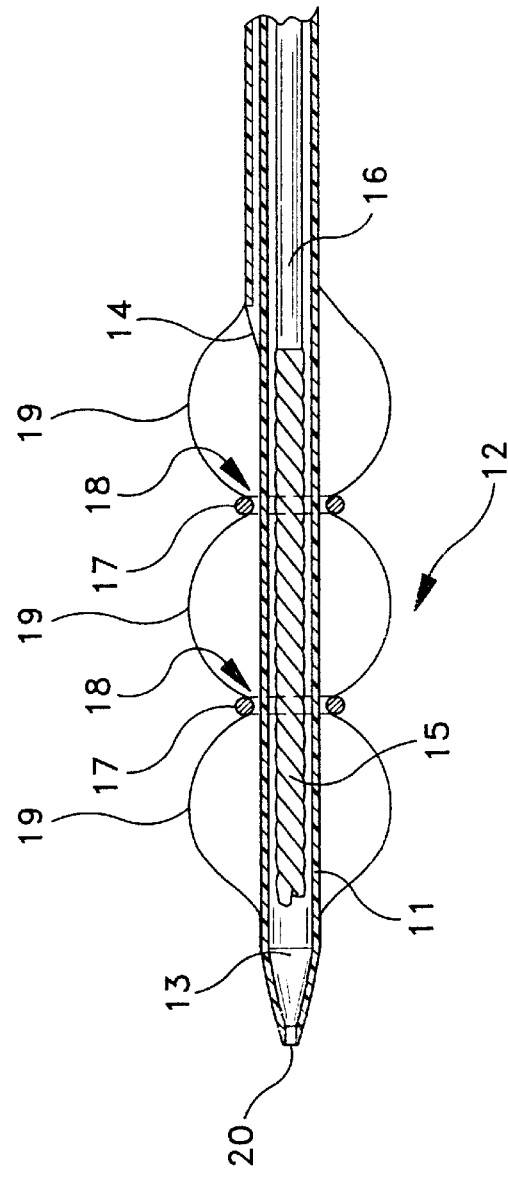

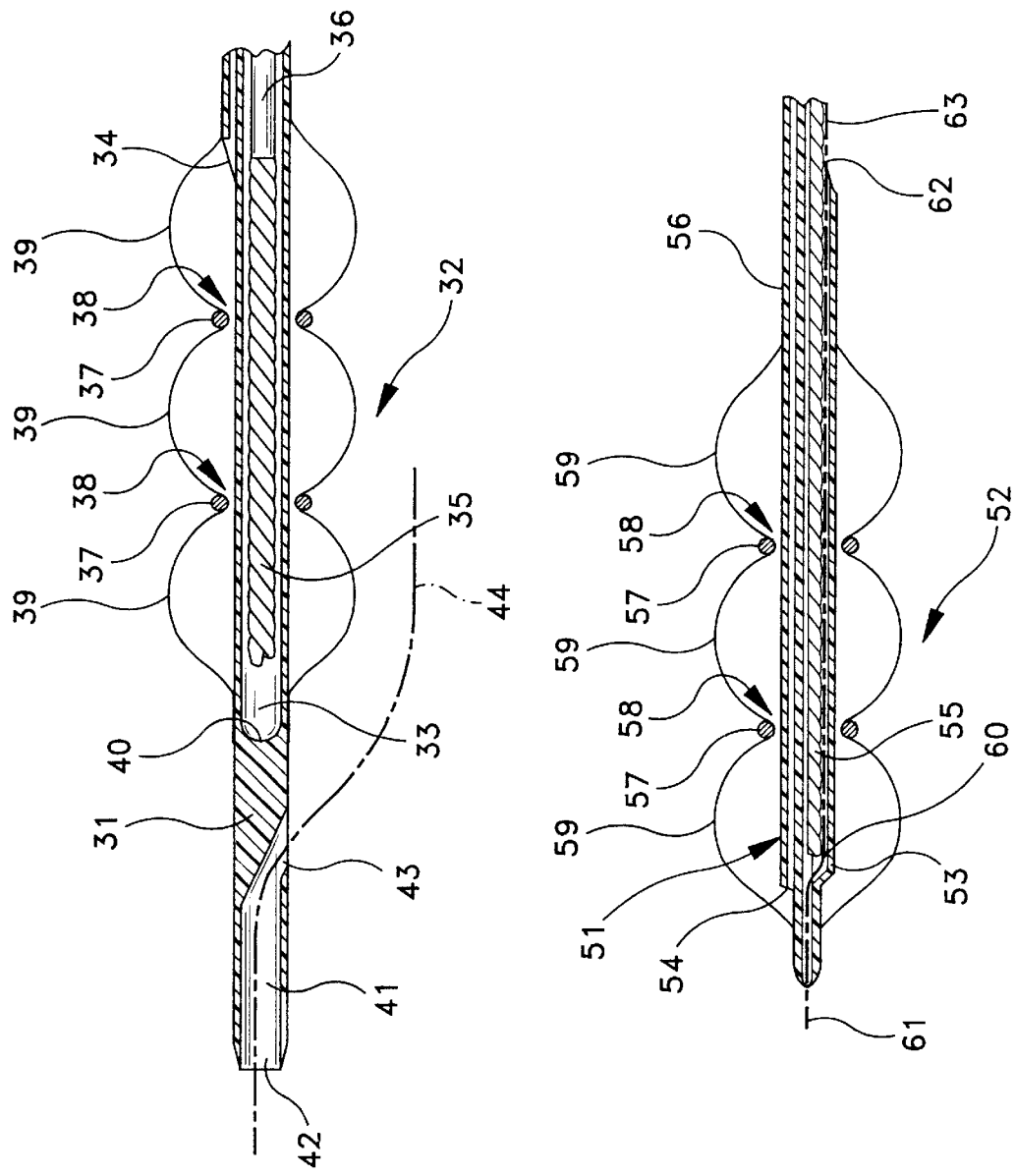

MEDICAL APPLIANCE WITH CENTERING BALLOON

This application is a continuation of U.S. patent application Ser. No. 08/492,503 now U.S. Pat. No. 5,976,106, filed Jun. 20, 1995, which claims priority to European Patent Application No. 94109858.4, filed Jun. 24, 1994.

BACKGROUND OF THE INVENTION

This invention relates to a medical appliance for the treatment of a portion of body vessel by ionizing radiation, comprising a catheter, an inflatable elongated balloon distally surrounding the catheter, and lumen means longitudinally extending through the catheter for positioning a radioactive radiation emitter within the balloon.

U.S. Pat. No. 5,213,561 describes a device for preventing restenosis after angioplasty comprising, among various embodiments, a catheter having a balloon at its distal end and a center core or tube in which a conventional guidewire is receivable. Particles or crystals of radioactive material are embedded in or mounted on the tube inside the balloon and a retractable shielding sleeve is slidable along the tube to cover the radioactive source, blocking exposure to radiation until it is shifted away. Such a structure is said to allow radiation of a vascular structure immediately following completion of angioplasty, without separately inserting a radiation source.

Standard dilatation balloons are not well suited to transport and to take up radioactive radiating sources because the center core or guidewire lumen tends to warp on the stretch inside the balloon, thereby forming an undulated line. The radioactive radiation source, however, has to be centered as exactly as possible inside the vessel in order to avoid the vessel wall being burned.

The document DE-9102312.2 describes balloon catheters for performing angioplasty procedures followed by radioactive irradiation to prevent restenosis. In a first embodiment, there is provided a catheter closed at its distal end and bearing a dilatation balloon which can be inflated by a fluid medium supplied via a lumen extending longitudinally of the catheter; a radioactive seed affixed to the end of a guidewire may be inserted into the catheter lumen to be brought into the site of angioplasty while the balloon is inflated; according to a variant, the lumen of the catheter may be separated in two parallel channels by a longitudinally extending intermediate wall, one of the channels being for insertion of the fluid for inflating the balloon and the other for insertion of a guidewire having the radioactive seed affixed at its end. In a second embodiment, the catheter comprises an additional channel centered in the catheter lumen by means of two longitudinally extending intermediate walls; the catheter lumen is thus divided into three channels, of which the central channel is for insertion of a radioactive pin affixed at the end of a guidewire and the lateral channels for balloon inflation and for supplying drugs into the blood vessel, respectively. In a third embodiment, the catheter bears two balloons at a distance from one another and which can be inflated separately; the catheter also comprises a central channel centered in the catheter lumen by means of four longitudinally extending walls defining four channels surrounding the central channel; two of the surrounding channels are respectively opening into the balloons for inflation thereof, and the two other surrounding channels are respectively opening between the two balloons to allow injection of drugs in the vessel area comprised between the two balloons; the document indicates that a radioactive seed affixed to the distal end of a guidewire may be placed in the lowest of the surrounding channels; the document also indicates that the radioactive source may be placed in the central channel, further outlining that, as with the second embodiment, the radioactive source may even be driven out of the catheter to directly irradiate the vessel. Apart from the fact that this document does not consider any particular centering of the radioactive source in the body vessel, its various configurations do not allow such a centering.

In the first embodiment of this document DE-9102312.2 no measures are described which would ensure circumferentially uniform radiation impact on the vessel wall and the radial position of the irradiation source is merely determined by gravity, whereby warping of the catheter lumen upon inflation of the balloon will add to the unevenness of radiation distribution in the vessel. In the second embodiment, any warping upon inflation of the balloon will be fully uncontrollable because of the different reactions of the main channel, additional channel and longitudinal walls of the catheter to the stresses resulting from the stretch inside the balloon; this of course makes it impossible to know where and how the radioactive radiation will be distributed in the vessel. In the third embodiment, the situation shows the same drawbacks as for the second embodiment, with some more uncertainty resulting from the additional channels.

The document DE-3620123-A1 discloses an apparatus for measuring and irradiating body cavities which permits the placing and positioning of a light conductor at the center of a cavity in order to achieve homogeneous lighting thereof via a dispersing agent.

To this effect, a light conductor is located in a tubular catheter surrounded by two optically transparent centering flexible balloons at a distance from each other and which are inflated by a dispersing agent in order to have them rest against the wall of the body cavity. The portion of the catheter which is located between the balloons is stiffer than the rest of the catheter to avoid modification of the distance between the two balloons, for instance due to curving of the catheter. The system is said to be usable for a blood vessel, and the two balloons are occlusion balloons. Occlusion balloons have to be resilient to safely fulfill their task in a vessel of unknown exact shape and size. Because of this resiliency, occlusion balloons can not be used simultaneously as dilatation balloons. Resilient balloons would overstretch the vessel wall when used with the higher pressures that are required for a successful angioplasty. Of course the doctor has control over the inflation pressure with resilient balloons same as with dilatation balloons, but this is not sufficient for safe angioplasty. With a resilient balloon the doctor has no control over the inflated diameter or over the shape to which the balloon is inflated. Of course, with this apparatus the source could be centered if the balloons are close together, but the additional weldings of two balloons close together make the catheter more complicated and expensive. Furthermore, the added weldings reduce the flexibility of the catheter which is necessary to maneuver it through tortuous vessels and to use it in tortuous vessels.

The purpose of this invention is to improve the conditions of radioactive radiation treatment of body vessels by proposing a medical appliance with inflatable balloon for a vessel wall radiation which is uniform around the vessel, an appliance that is highly versatile, simple to manufacture and easy to use.

SUMMARY OF THE INVENTION

In the present invention, a waist centers the lumen containing the radioactive radiation emitter inside the body vessel at least at the location thereof and substantially eliminates any undulated shape which may be taken by the catheter or lumen containing the radioactive radiation emitter. The stretch occurring upon inflation of the balloon therefore does not affect the positioning of the radioactive radiation emitter within the body vessel. And the appliance may retain a good flexibility allowing its maneuver and use in tortuous and/or narrow vessels.

Specifically, it becomes possible to improve dosage control of the radioactive radiation with regard to the distance between radioactive source and vessel wall, whereby overdosage because of too narrow distance and underdosage because of too wide distance to the vessel wall is avoided, and the impact of radiation on the vessel wall is essentially uniform.

The waist may be created by belt means which may be regularly or irregularly spaced from one another over the length of the balloon in order to match any structural configuration and warping tendency of the catheter and balloon assembly.

For inexpensive fitting of existing balloon catheters, the belt means may be made of surgical thread, possibly surgical thread tied with a knot.

To modulate the centering of the catheter within the balloon, the belt means may be made of molded rings, the length and thickness of which will be chosen as a function of the strength needed to counteract the warping tendency of the catheter.

For safety purposes, the lumen means may have a narrowed distal end whereby the catheter may be normally guided along a guidewire while the radioactive radiation means may be sufficiently thick for not passing through the narrowed distal end. Similarly the lumen means may be closed distally.

The waist or belted balloon catheter may be adapted to several practical configurations, for example to allow use of the technology known under the trade mark MONORAIL. In this case, the lumen means may be closed distally, and the catheter may further comprise a guidewire lumen with an entry and an exit distal of the balloon, which advantageously results in a two lumen catheter construction which will be easily centered within the balloon by the belt means. The catheter may also comprise a guidewire lumen with an entry distal of the balloon and an exit proximal of the balloon, the three lumen catheter so achieved being also correctly centered within the balloon by the belt means.

In sum, the present invention relates to a medical appliance for the treatment of a portion of body vessel by ionizing radiation with a catheter, an inflatable elongate balloon distally surrounding the catheter, and lumen means longitudinally extending through the catheter for positioning a radioactive radiation emitter within the balloon. A waist on said balloon essentially centers the catheter within the balloon. The belt means may create the waist, and may be regularly spaced from one another over the length of the balloon or irregularly spaced from one another over the length of the balloon. The belt means may be made of surgical thread, which may be tied with a knot. The belt means may be made of molded rings. The belt means may be affixed to the balloon, such as by adhesion. The lumen means may have a narrowed distal end, and may be closed distally. The catheter may further have a guidewire lumen with an entry and an exit distal of the balloon, or a guidewire lumen with an entry distal of the balloon and an exit proximal of the balloon.

In an alternative embodiment, the present invention relates to a catheter that may have an elongate tubular member having a distal portion with an outside diameter; an at least partially expandable balloon configured on the distal portion of the tubular member, the balloon having a distal end, a proximal end, and at least one intermediate segment therebetween; and balloon expansion restriction means for limiting the expansion of at least one intermediate segment so that the segment does not substantially expand. The catheter may also have an elongate tubular member; and a balloon configured on the tubular member, the balloon having a proximal segment, a distal segment and at least one intermediate segment wherein the proximal and distal segments are inflatable to diameters which are greater than the inflatable diameters of the at least one intermediate segment. In another embodiment, the catheter may have an elongate tubular member having an outside diameter; an at least partially expandable balloon configured on the tubular member; a first zone on the balloon, inflatable to a first inflated diameter; and a second zone on the balloon, inflatable to a second diameter; wherein the second diameter is essentially the same diameter as the outer diameter of the tubular member.

DESCRIPTION OF THE DRAWINGS

These and other objects will become readily apparent from the following detailed description with reference to the accompanying drawings which show diagrammatically and by way of example only four embodiments of the invention.

FIGS. 1 to 4 are respectively longitudinal cuts of the first, second, third and fourth embodiments.

In all the embodiments shown only the portions of the medical appliance which have to be located at the site of treatment have been depicted, the other portions of the embodiments being devised as currently practiced in the art. The portion of the body vessel where treatment occurs has not been shown.

DESCRIPTION OF THE PREFERRED EMBODIMENT

The described materials are specifically directed to percutaneous transluminal angioplasty. This is however not limitative and the invention is also applicable to materials directed to the treatment of other body vessels.

The first embodiment of FIG. 1 is a balloon catheter comprising a catheter tube 1 surrounded distally by an elongated inflatable balloon 2. The balloon 2 is proximally and distally affixed, for instance welded, to the catheter tube 1 as commonly practiced in the art. Throughout the catheter tube 1 is a longitudinal lumen 3 which is adapted to position a guidewire and/or a radioactive radiation emitter within the balloon 2. The catheter 1 comprises a second lumen 4 for directing inflation fluid into the balloon 2. The balloon 2 is shown in inflated condition at the location of a stenosis (not shown) of a blood vessel such as a coronary artery. A radioactive radiation emitter 5, in this example in the form of a coiled filament, is affixed to the distal end of a guidewire 6, and this coiled filament is sized for a substantial sliding fit within the lumen 3 of catheter tube 1.

Two belt means 7 creating a waist, in this example molded rings regularly spaced from one another over the length of the balloon, are mounted on the balloon 2 for essentially centering the catheter 1 within the balloon 2. The belt means 3 are affixed to the balloon 2, for example adhesively adhered thereto, and they squeeze the balloon 2 down to nearly the diameter of the catheter thereby leaving a small passage 8 for the inflation fluid supplied to the balloon 2 via lumen 4. The belt means 7 divide the balloon 2 into sections 9 which are substantially similar and they assure a close center fit of the catheter 1 within the balloon 2 at least at the respective locations of the lace, thereby eliminating, or at least strongly minimizing, the effects of catheter warping upon inflation of the balloon. The lumen 3 and radioactive radiation emitter 5 in sliding fit therein are thus essentially centered inside the vessel, at least at the locations of the lace.

The second embodiment of FIG. 2 is also a balloon catheter comprising a catheter tube 11 distally surrounded by an elongated inflatable balloon 12 affixed to the catheter as usual in the art. Throughout the catheter tube 11 is a longitudinal lumen 13 adapted to position a guidewire and/or a radioactive radiation emitter within the balloon 12. At the distal end of the catheter 11, the lumen 13 has a narrowed distal end 20 the purpose of which is to allow passage of a guidewire while preventing passage of a radioactive radiation emitter which is made a little thicker than the guidewire. The catheter comprises a second lumen 14 for supplying inflation fluid to the balloon 12. A radioactive emitter 15, also in the form of a coiled filament, is affixed to the distal end of a guidewire 16, this coiled filament being sized for a substantial sliding fit within the lumen 13 of catheter tube 11.

As for the embodiment of FIG. 1, two belt means 17 creating a waist are formed of molded rings which are regularly spaced from one another over the length of the balloon and which are mounted on the balloon and adhesively adhered thereto for essentially centering the catheter 11 within the balloon 12. These belt means 17 squeeze the balloon 12 down to nearly the diameter of the catheter in order to leave a small passage 18 for the inflation fluid supplied to the balloon via lumen 14. The belt means 17 also divide the balloon 12 into sections 19 which are substantially similar, and they assure a close center fit of the catheter 11 within the balloon 12 at least at the respective locations of the lace to substantially eliminate the effects of catheter warping upon inflation of the balloon, whereby the lumen 13 and radioactive radiation emitter 15 in sliding fit therein will be essentially centered inside the vessel, at least at the locations of lace.

The third embodiment of FIG. 3 is a balloon catheter which makes use of the MONORAIL (trade mark) catheter technology. This balloon catheter comprises a catheter tube 31 distally surrounded by an elongated balloon 32 affixed to the catheter tube. Within the catheter tube 31 is a longitudinal lumen 33 preferably distally closed at a location 40 substantially corresponding to the distal end of balloon 32, which lumen 33 is for allowing passage of a guiding wire 36 provided with a distal radioactive radiation emitter 35 the travel of which is limited for safety purposes by the closed distal end 40 of lumen 33. The catheter also comprises a lumen 34 for supplying inflation fluid to the balloon 32. The catheter 31 further comprises a guidewire lumen 41 with an entry 42 and exit 43 distal of the balloon 32 for accommodating a guidewire 44 in the MONORAIL (trade mark) configuration.

As for the previous embodiments, a waist is created by two belt means 37 which are formed of molded rings regularly spaced from one another over the length of the balloon 32 and which are mounted on the balloon and adhesively secured thereto for essentially centering the catheter 31 within the balloon 32. Belt means 37 squeeze the balloon 32 to nearly the diameter of the catheter 31 and thereby leave a small passage 38 for the inflation fluid ejected by lumen 34. Belt means 37 divide the balloon 32 into similar sections 39 and they assure a close center fit of catheter 31 within the balloon 32, at least at the respective locations of the lace. As in the previous embodiments, this structure substantially eliminates the effects of catheter warping upon inflation of the balloon and therefore the lumen 33 and radioactive radiation emitter 35 in sliding fit therein will be essentially centered in the body vessel, at least at the locations of lace.

The fourth embodiment of FIG. 4 also makes use of the MONORAIL (trade mark) technology. This balloon catheter comprises a catheter tube 51 distally surrounded by an elongated balloon 52. Within catheter tube 51 is a longitudinal lumen 53 for allowing passage of a guiding wire 56 provided with a distal radioactive radiation emitter in the form of a filament 55 sized for a sliding fit into lumen 53. The catheter also comprises a lumen 54 for supplying inflation fluid to the balloon 53 and a guidewire lumen 60, preferably symmetrical to lumen 54 with respect to the longitudinal axis of the catheter, having an entry 61 distal of the balloon 52 and an exit 62 proximal of the balloon 52 for accommodating a guidewire 63 in the MONORAIL (trade mark) configuration.

This embodiment also comprises a waist made of two belt means 57 formed of molded rings regularly spaced from one another over the length of the balloon 52 and adhesively secured on the balloon for essentially centering the catheter 51 within the balloon 52. Belt means 57 squeeze the balloon 52 to nearly the diameter of catheter 51 thereby leaving a small passage 58 for the inflation fluid arising from lumen 54. Belt means 57 divide the balloon 52 in three similar sections 59, thereby assuring a close center fit of catheter 51 within the balloon at least at the respective site of the lace, a structure which substantially eliminates the effects of catheter warping upon inflation of the balloon, despite the three lumen construction. The lumen 53 and radioactive radiation filament 55 in sliding fit therein will therefore be essentially centered in the body vessel, at least at the locations of lace.

Variants may be envisaged.

For instance, the belt means may be made of surgical thread; they may be made possibly of surgical thread tied with a knot.

The belt means may also be made of molded rings of different length and/or thickness.

The belt means may be irregularly spaced from one another over the length of the balloon. Within this frame, it is possible to have a repartition of belt means providing a central section of the balloon which is longer than a proximal and a distal section thereof.

It is possible to have more than two belt means to constitute the waist in case of long balloon configurations as well as it is possible to have only one belt means forming a waist in case of relatively short balloon configurations.

The belt means may be simply squeezing the balloon, without being affixed thereto. They may also be affixed to the balloon by welding.

And of course, the radioactive radiation emitter may be of any shape, configuration or material, other than the coil or filament described.

What is claimed is:

1. A balloon catheter system for treatment of a portion of a blood vessel by ionizing radiation, comprising:
   an elongate radiation device having a distally disposed ionizing radiation emitter;
   a catheter shaft having a radiation device lumen sized to receive the elongate radiation device therein, the radiation device lumen extending from a proximal end of the shaft to a distal end of the shaft; and a balloon disposed about a distal portion of the shaft, the balloon having at least three lobes such that the catheter is substantially centered in the blood vessel, despite curvature thereof.

2. A balloon catheter system as in claim 1, wherein the balloon comprises a single balloon.

3. A balloon catheter system as in claim 1, wherein the lobes are defined by waists on either side thereof.

4. A balloon catheter system as in claim 3, wherein the waists are defined by belts.

5. A balloon catheter system as in claim 1, wherein the shaft includes an inflation lumen for inflating and deflating the balloon.

6. A balloon catheter system as in claim 5, wherein the shaft includes a guidewire lumen sized to receive a guidewire.

7. A balloon catheter system as in claim 6, wherein the guidewire lumen extends through the balloon.

8. A balloon catheter system as in claim 6, wherein the guidewire lumen has a proximal opening disposed distal of a proximal end of the shaft.

9. A balloon catheter system as in claim 6, wherein the guidewire lumen has a proximal opening disposed distal of the balloon.

10. A balloon catheter system as in claim 1, wherein the radiation device lumen has a closed distal end.

11. A balloon catheter system as in claim 1, wherein the radiation device lumen has an open distal end.

12. A balloon catheter system as in claim 11, wherein the open distal end of the radiation device lumen has a reduced diameter.

13. A balloon catheter system for treatment of a portion of a blood vessel by ionizing radiation, comprising:
    an elongate radiation device having a distally disposed ionizing radiation emitter;
    a catheter shaft having a radiation device lumen sized to receive the radiation device, the radiation device lumen extending from a proximal end of the shaft to a distal end of the shaft; and
    a balloon disposed about a distal portion of the shaft, the balloon having a proximal waist, a distal waist, and at least two intermediate waists such that the shaft is substantially centered in the balloon, despite curvature thereof.

14. A balloon catheter system as in claim 13, wherein the balloon comprises a single balloon.

15. A balloon catheter system as in claim 13, wherein the waists are defined by belts.

16. A system for treatment of a portion of a blood vessel by ionizing radiation, comprising:
    an ionizing radiation emitter; and
    a balloon catheter, the balloon catheter comprising a shaft having a lumen sized to receive the ionizing radiation emitter and a balloon disposed about a distal portion of the shaft, the balloon having at least three lobes such that the catheter is substantially centered in the blood vessel, despite curvature thereof.

17. A system for treatment of a portion of a blood vessel by ionizing radiation, comprising:
    an ionizing radiation emitter; and
    a balloon catheter, the balloon catheter comprising a shaft having a lumen sized to receive the ionizing radiation emitter and a balloon disposed about a distal portion of the shaft, the balloon having a proximal waist, a distal waist, and at least two intermediate waists such that the shaft is substantially centered in the balloon, despite curvature thereof.

18. A system as in claim 16, wherein the ionizing radiation emitter comprises an elongate filament.

19. A system as in claim 17, wherein the ionizing radiation emitter comprises an elongate filament.

20. A method for treatment of a portion of a blood vessel by ionizing radiation, comprising the steps of:
    providing an ionizing radiation emitter;
    providing a balloon catheter, the balloon catheter comprising a shaft having a lumen sized to receive the ionizing radiation emitter and a balloon disposed about a distal portion of the shaft, the balloon having at least three lobes;
    inserting the balloon catheter into the blood vessel;
    inflating the balloon such that the catheter is substantially centered in the blood vessel, despite curvature thereof and
    inserting the ionizing radiation emitter into the lumen of the catheter for treatment of the blood vessel.

21. A method for treatment of a portion of a blood vessel by ionizing radiation, comprising the steps of:
    providing an ionizing radiation emitter;
    providing a balloon catheter, the balloon catheter comprising a shaft having a lumen sized to receive the ionizing radiation emitter and a balloon disposed about a distal portion of the shaft, the balloon having a proximal waist, a distal waist, and at least two intermediate waists such that the shaft is substantially centered in the balloon;
    inserting the balloon catheter into the blood vessel;
    inflating the balloon such that the catheter is substantially centered in the blood vessel, despite curvature thereof; and
    inserting the ionizing radiation emitter into the lumen of the catheter for treatment of the blood vessel.

22. A centering catheter for intravascular delivery of a radiation source for administering ionizing radiation to a blood vessel, the centering catheter comprising:
    an elongate shaft having a proximal portion, a distal portion and a radiation source lumen extending therebetween, the elongate shaft further having a guidewire lumen and an inflation lumen;
    an inflatable balloon disposed on a distal portion of the elongate shaft, wherein the balloon, when viewed in longitudinal cross-section, defines three or more lobes for substantially centering the catheter in the blood vessel despite curvature thereof.

23. A centering catheter as in claim 22, wherein the source lumen is adapted to receive the radioactive source therein, and wherein the lobes substantially center the source lumen and thus the radiation source within the vessel.

24. A centering catheter as in claim 23, wherein the lobes are defined by waists.

25. A centering catheter as in claim 24, wherein the waists are regularly spaced from one another along the length of the balloon.

26. A centering catheter as in claim 24, wherein the waists are formed by belt means.

27. A centering catheter as in claim 26, wherein the belt means are made of molded rings.

28. A centering catheter as in claim 26, wherein the belt means are affixed to the balloon.

29. A centering catheter as in claim 28, wherein the belt means are adhesively affixed to the balloon.

30. A centering catheter for the administration of ionizing radiation to a blood vessel wall, comprising:

an elongate shaft having a proximal end, a distal end and a radiation source lumen extending therebetween, the elongate shaft further having a guidewire lumen and an inflation lumen; and a balloon disposed about the distal end of the elongate shaft, wherein the balloon, when in an inflated state, forms multiple contact points with the vessel wall as viewed from a longitudinal cross-section for substantially centering the catheter in the blood vessel despite curvature thereof.

* * * * *

UNITED STATES PATENT AND TRADEMARK OFFICE
CERTIFICATE OF CORRECTION

PATENT NO.    : 6,616,629 B1                                                Page 1 of 1
DATED         : September 9, 2003
INVENTOR(S)   : V. Verin et al.

It is certified that error appears in the above-identified patent and that said Letters Patent is hereby corrected as shown below:

Title page,
Item [56], References Cited, FOREIGN PATENT DOCUMENTS, please insert, in appropriate order, the following reference:
-- EP    0 080 436 A1    6/1983 --
-- EP    0 813 894 A2    12/1997
   EP    0 826 395 A1    3/1998 --
-- WO    WO 89/02763    4/1989
   WO    WO 91/08013    6/1991 --

Column 8,
Line 19, after "thereof" insert -- ; --

Signed and Sealed this

Twenty-third Day of March, 2004

JON W. DUDAS
*Acting Director of the United States Patent and Trademark Office*